United States Patent
von der Heyde

[19]

[11] Patent Number: 5,887,304
[45] Date of Patent: Mar. 30, 1999

[54] APPARATUS AND METHOD FOR PREVENTING SUDDEN INFANT DEATH SYNDROME

[76] Inventor: Christian P. von der Heyde, 182 Great Hill Rd. Extension, East Sandwich, Mass. 02537

[21] Appl. No.: 882,388

[22] Filed: Jul. 10, 1997

[51] Int. Cl.⁶ .................................................. A47C 21/00
[52] U.S. Cl. ...................................... 5/726; 5/724; 5/423
[58] Field of Search ............................... 5/641, 423, 722, 5/723, 724, 726, 691

[56] References Cited

U.S. PATENT DOCUMENTS

| | | | |
|---|---|---|---|
| 1,142,876 | 6/1915 | Davis | 5/910 X |
| 3,268,064 | 8/1966 | Figman | 5/423 X |
| 3,681,797 | 8/1972 | Messner | 5/910 X |
| 3,742,528 | 7/1973 | Munch | 5/723 |
| 4,057,861 | 11/1977 | Howorth | 5/423 X |
| 5,463,785 | 11/1995 | McKeel | 5/724 X |
| 5,493,742 | 2/1996 | Klearman | 5/726 X |
| 5,561,875 | 10/1996 | Graebe | 5/423 |
| 5,652,987 | 8/1997 | Fujita | 5/726 |

*Primary Examiner*—Michael F. Trettel
*Attorney, Agent, or Firm*—Wolf, Greenfield & Sacks, P.C.

[57] ABSTRACT

An apparatus and method for preventing asphyxiation of an infant due to breathing of exhaled carbon dioxide. A mattress with optional mattress pad provides an even air flow that removes exhaled carbon dioxide that accumulates at or near the surface of the mattress or mattress pad. The infant may be located anywhere on the surface of the mattress or mattress pad as the even air flow disperses carbon dioxide across the entire surface. In a preferred embodiment, the even air flow is accomplished by forcing air into a cavity, or plenum chamber, in the body of the mattress which air distributes equally to air flow holes on the top surfaces of the mattress and mattress pad. Optional temperature regulating or medicine dispensing devices respectively heat or cool the air flow, or introduce medicine into the air flow. In another embodiment, the mattress is itself a mattress pad. That is, the mattress pad provides an even air flow as described and may be placed on the sleeping surface of a conventional mattress.

21 Claims, 6 Drawing Sheets

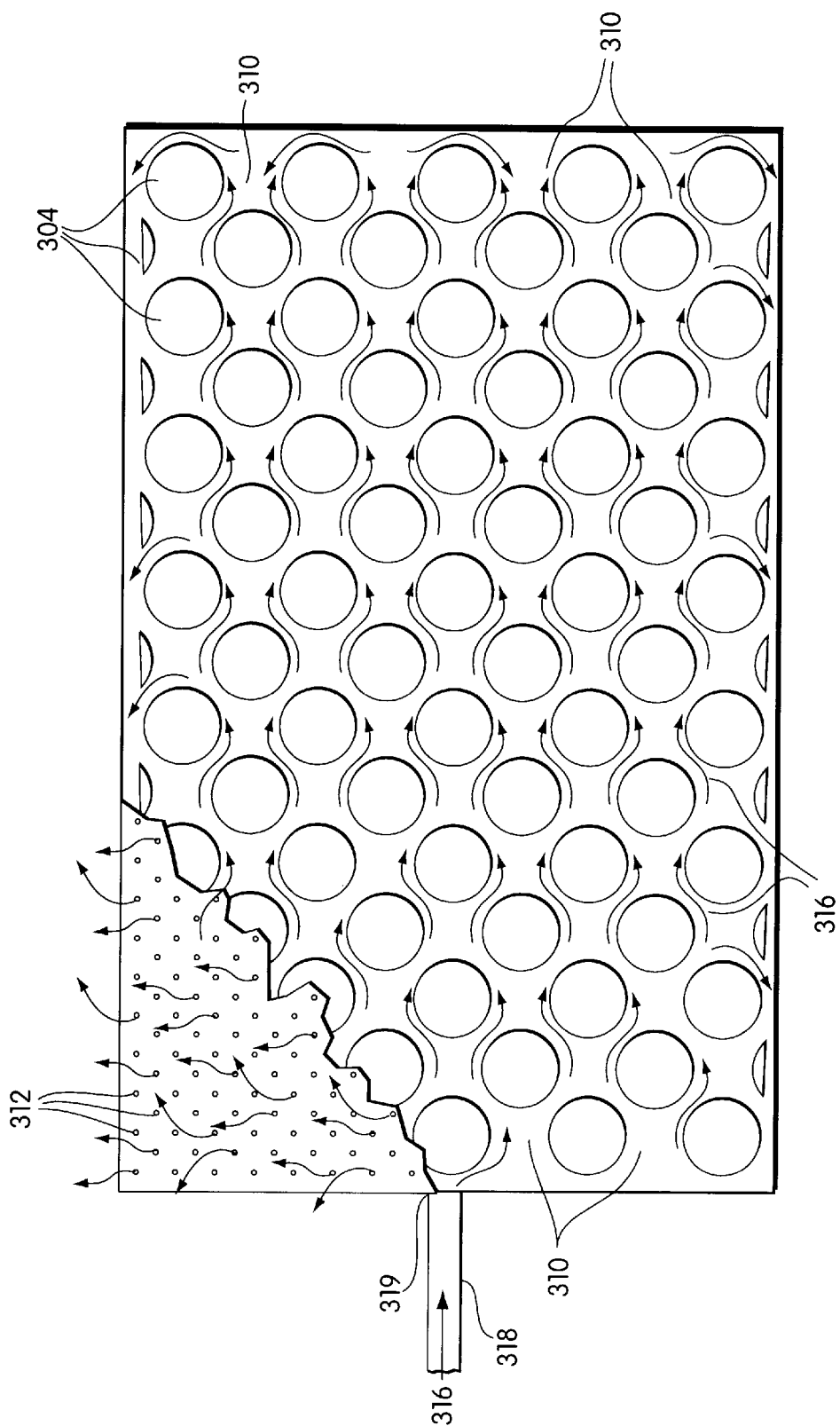

APPARATUS AND METHOD FOR PREVENTING SUDDEN INFANT DEATH SYNDROME

FIELD OF THE INVENTION

This invention generally relates to apparatuses and methods for preventing sudden infant death syndrome, and more particularly to mattresses and pads that remove exhaled carbon dioxide from the vicinity of a sleeping infant's mouth to prevent asphyxiation.

BACKGROUND OF THE INVENTION

Sudden Infant Death Syndrome (SIDS) claims the lives of thousands of infants in the United States each year. These infants generally appear to be normal and healthy, but succumb without warning in their cribs. The cause of SIDS is not known, and thus there is no certain means of preventing these tragedies. Medical specialists have, however, advanced several theories to explain the onset of SIDS. U.S. Pat. No. 5,483,711 issued to Hargest et al. reviews these theories, provides statistics regarding the impact of SIDS in the United States, and explains the advantage of placing an infant on its stomach for rest or sleep to prevent choking on regurgitated fluids. This advantage may be accentuated in the case of a premature or newborn infant with relatively undeveloped lungs. However, placing the infant on its stomach has certain drawbacks. As noted in Hargest, one theory regarding the cause of SIDS is that an infant sleeping or resting on its stomach, and thus with its mouth near the mattress or mattress pad of its crib, inhales the carbon dioxide products of breathing that have accumulated near the top surface of the mattress or mattress pad resulting in "carbon dioxide poisoning." This result may alternatively be described as suffocation due to an insufficient amount of oxygen in the carbon-dioxide rich air near the infant's mouth. The presence of bedding may contribute to such accumulation and thus contribute to the possibility of suffocation by the infant.

As a result, there are reasons to conclude that SIDS may be prevented by avoiding the accumulation of carbon dioxide near the top surface of the mattress or mattress pad of an infant's crib. Known apparatuses for attempting to prevent such accumulation, and in some cases for attempting to provide a fresh flow of air or oxygen, include that of Hargest and also the mattresses disclosed in U.S. Pat. No. 5,546,618 issued to Beedy et al., U.S. Pat. No. 4,536,906 issued to Varndell et al., and U.S. Pat. No. 3,339,216 issued to Ormerod.

These known mattresses and mattress pads, however, suffer from the limitation, among others, that the mechanism or method for preventing the accumulation of carbon dioxide or introducing fresh air is localized in the region where the infant's mouth is expected to be located. Thus, such mattresses or mattress pads are ineffective for their intended use if the infant moves its position so that its mouth is no longer situated near the region where carbon dioxide is discharged. Moreover, this localization prevents the achievement of an even temperature over the top surface of the mattress or mattress pad if the discharged air is heated or cooled. Also, the flow of air over the mattress top surface may be irregular or difficult to regulate. Such undesirable temperature gradients and drafts may be addressed by covering the infant with a blanket or other bedding, but the use of such bedding may, as already noted, introduce an additional mechanism that causes carbon dioxide accumulation.

Accordingly, it is a general object of the present invention to overcome the drawbacks of prior art apparatuses and methods, such as by preventing the accumulation of carbon dioxide across the entire top surface of the mattress or mattress pad, maintaining an even flow of air over the top surface of the mattress or mattress pad, maintaining an even temperature over the mattress or mattress pad top surface, and/or avoiding the need for bedding.

SUMMARY OF THE INVENTION

The foregoing and other objects, features and advantages of the present invention are achieved in a mattress which includes a plurality of passageways distributed generally evenly over the entire top surface of the mattress. Each of these passageways is coupled to a system for generally equally distributing air from a source of air or other gas to each of the passageways. In a preferred embodiment, a plenum chamber is provided in the center of the mattress which is in gaseous communication with the source of air. Each of the air passageways is then in gaseous communication with the plenum chamber which equally distributes gas to each of the passageways.

In another aspect of the invention, a mattress pad may be provided. The mattress pad also includes air flow holes or passageways evenly distributed over generally the entire top surface of the pad. In one embodiment of this aspect of the invention, alignment features are provided such that the holes or passageways in the mattress pad are aligned with similar passageways in the mattress so that a flow of air is provided unimpeded through the top surface of the mattress and mattress pad to provide a continuous and evenly distributed flow of air over the entire top surface of the mattress pad where the infant rests. The alignment feature typically comprises a plurality of flexible pegs in the top surface of the mattress which seat in correspondingly formed holes or recesses in the mattress pad.

In other aspects of the invention, an air pump may be utilized to pump air to the mattress, a heater or cooler may be used to regulate the temperature of the air, and a medicine dispenser may be used to introduce medicine into the air flow. Alternatively, a suction device may be coupled to the air stream to remove gases from the top surface of the mattress.

In yet another aspect of the invention, the source of air is connected directly to a top surface of a mattress pad that has a plurality of bumps or projections. A plenum chamber is formed between the top surface of the pad and the outer membrane of the mattress pad. The outer membrane has a plurality of holes, in direct gaseous connection with the plenum chamber, generally evenly distributed over the entire top surface. As air is pumped into the mattress pad, air pressure builds in the plenum chamber between the outer membrane and the top surface of the mattress pad, and air escapes through the plurality of holes in the outer membrane. A heater or cooler may be used to regulate the temperature of the air, and a medicine dispenser may be used to dispense medicine into the air flow. The direction of air flow may be reversible. In one aspect, the outer membrane of the mattress pad is attached to the mattress pad by a connecting apparatus, such as a zipper, and the outer membrane may be removed to facilitate cleaning.

In the method of the present invention, air is uniformly distributed to substantially the entire top surface of the mattress or mattress pad to provide a fresh flow of oxygen to the infant, and to prevent the accumulation of carbon dioxide adjacent to the infant. This method assures that the infant is supplied with sufficient oxygen no matter where the infant migrates over the course of time while sleeping. In addition, the temperature of the air directed to the top surface of the mattress may be controlled, so that the air temperature surrounding the infant is controlled to obviate the use of bedding, thereby reducing the likelihood of an undesirable accumulation of carbon dioxide.

BRIEF DESCRIPTION OF THE DRAWINGS

The objects, features and advantages of this invention will be more clearly appreciated from the following detailed description when taken in conjunction with the accompanying drawings, in which:

FIG. 7 is a cut-away top plan view of the mattress pad of FIG. 5.

DETAILED DESCRIPTION

Figure 1:
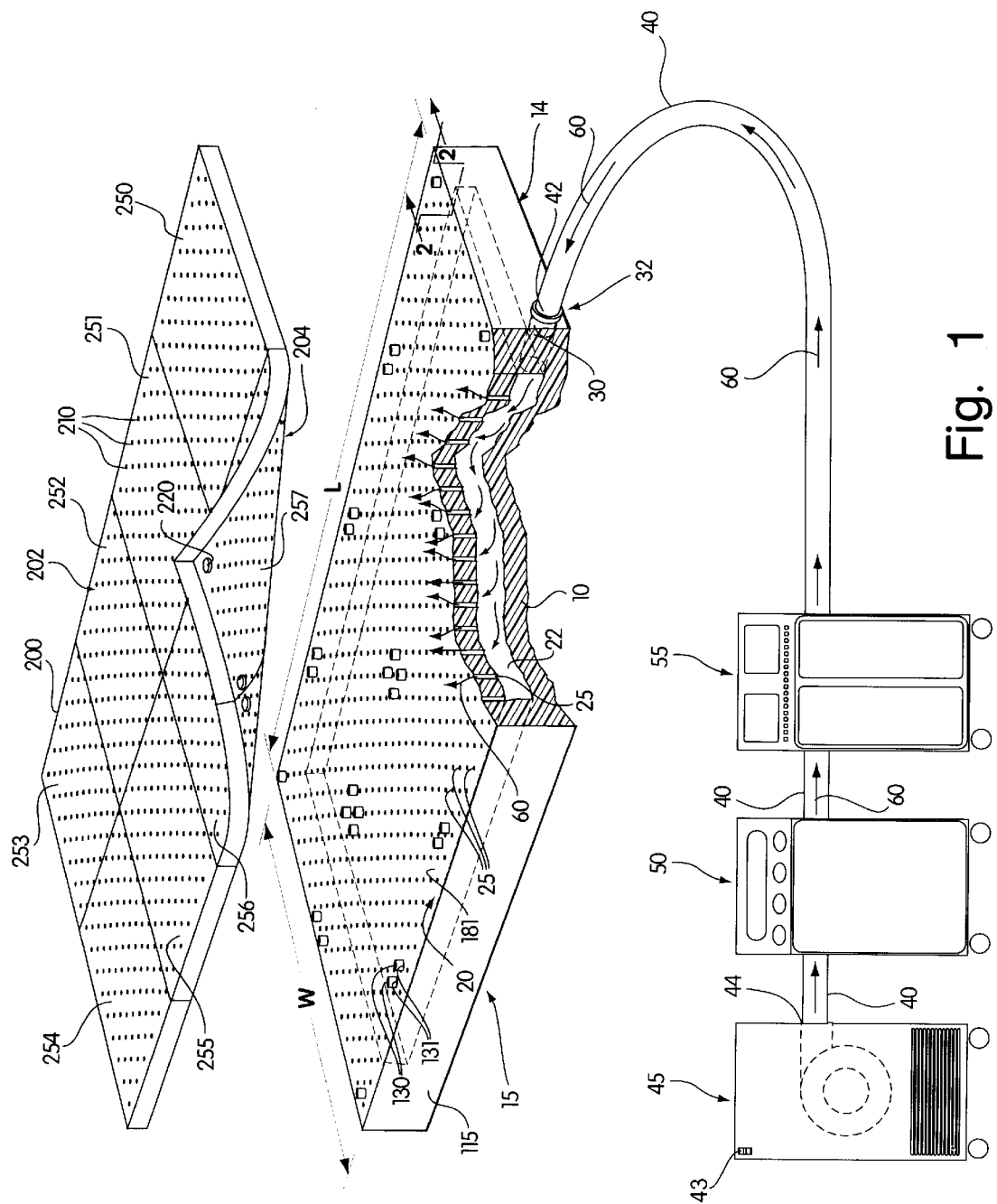
FIG. 1 is a perspective cut-away view of a partial schematic of one embodiment of the present invention including a mattress and mattress pad.

The detailed description below should be read with reference to the accompanying drawing figures in which like reference numerals indicate like structures. The examples included in the description are intended merely to be illustrative.

The mattress of this invention employs a novel architecture including a plurality of air flow holes evenly distributed over the entire upper sleeping surface of the mattress. Apparatus is provided to evenly distribute air to each of the air flow holes. The preferred mattress pad of this invention has air flow holes that may be aligned with the air flow holes of the mattress. As used herein, the word "air" will be understood, unless the context otherwise requires, to include a mixture of air and oxygen or another gas in any ratio including, for example, pure air or pure oxygen. An air pump or suction device may be used, respectively, to push a flow of air into the plenum and thence through the air flow holes to and beyond the top surface of the mattress or mattress pad, or to suck air from such surface and thence through the plenum. In the case of an air pump to push air, an optional heater or cooler may be used to regulate the temperature of the air, and a medicine dispenser may be used to introduce medicine into the air flow, where the word "medicine" is understood to refer broadly to any medicine, gas including oxygen, medicated vapor, or other substance or treatment that adds to, alters, or affects the air. The architecture of a preferred embodiment of the invention will now be described in greater detail with reference to FIGS. 1 and 2.

With reference now to FIGS. 1 and 2, there is illustrated one embodiment of the mattress 10 of the invention having a lateral side 14, a bottom 15, and an upper mattress surface 20. A plenum chamber 22 is disposed within the mattress 10.

In a preferred embodiment, plenum chamber 22 extends approximately coextensively in length and width with the length L of the mattress surface 20 and the width W of the mattress surface 20. It is understood, however, that the plenum chamber 22 need not be approximately coextensive in length and width with the mattress surface.

As shown in FIG. 1, a plurality of air passageways 25, sometimes referred to as "mattress air flow holes," extend through the upper mattress surface 20. Each of passageways 25 is in direct gaseous communication with plenum chamber 22. Passageways 25 preferably are distributed over the entire extent of surface 20 and typically, although not necessarily, are evenly spaced from one another. In an embodiment in which the plenum chamber 22 is not approximately coextensive in length and width with the mattress surface, provision would be made to ensure that passageways 25 on the periphery of the mattress surface are in gaseous communication with the plenum chamber 22, such as by providing distribution elements such as tubing, manifolds, or secondary plenum chambers. The purpose of such additional distribution elements is to provide air flow to all areas of the surface of the mattress 20.

Passageways 25 typically are formed as holes cut in the upper surface of mattress 10 and extending into plenum chamber 22. These holes may be cut through the material after formation of the mattress, or formed during the molding of the mattress. In this preferred embodiment, it is not required that passageways 25 be lined to prevent the escape of air into any spaces between the surface of the mattress and the sides of the passageways. In other embodiments in which, for example, the material of mattress 10 is not relatively impermeable to air, passageways 25 may be so lined to ensure that all the air is conducted to the surface of mattress 10. In such alternative embodiments, the material lining the passageways 25 may be sewn or otherwise attached to material on the surface of the mattress, both for aesthetic and sanitary reasons. Alternatively, tubes (not shown) may be inserted through holes cut or formed in the mattress that extend into plenum chamber 22. These tubes would have to be sufficiently flexible to accommodate depression of the mattress and to prevent any injury to the child. A typical example of the material used to form these tubes would be a closed cell foam, or any other suitable material that is sufficiently resilient to absorb the weight of an infant, but would rebound upon rebounding of the mattress once the infant was removed from the surface of mattress 10.

An air port 30 and associated hose fitting 32 couple the plenum chamber 22 with an external source of air. It is understood that while the air port 30 is shown in this embodiment as disposed at lateral side 14 of mattress 10, it could readily be situated at any convenient location on any surface of mattress 10. Also shown schematically in FIG. 1 is a conduit such as a hose 40 attached at a first end 42 to the hose fitting 32. An air pump 45 is connected to a second end 44 of hose 40 so that air may be introduced into and pushed through hose 40 creating an air flow 60. The air pump may be any one of a number of known devices for circulating air, including the types described in Hargest at column 8, lines 46 through 59. In a preferred embodiment, heat canister 50 is disposed along the air flow 60 between the air pump 45 and mattress 10 for the purpose of heating or cooling the air as it passes through the canister. It is understood that heat canister 50 could be any one of a number of known devices for heating or cooling air, including the types described in Hargest at column 8, lines 66–67, and column 9, lines 1–14. In another embodiment, medicine canister 55 is disposed along the air flow 60 between the heat canister 50 and mattress 10 so that medicinal vapors or other medicine may be introduced into the air as it passes through the canister. It is understood that medicine canister 55 could be any of a number of known devices for introducing medicine into air, including the types described in Hargest at column 8, lines 59–65. It is further understood that the arrangement of the air pump 45, heat canister 50, and medicine canister 55 is not crucial and that the order may be rearranged so that, for example, the air pump 45 is positioned between the heat canister 50 and the medicine canister 55, or after the medicine canister 55, or the positions of the heat canister 50 and the medicine canister 55 could be reversed. The order shown in FIG. 1 may be preferable because of the possibility that air that is heated or contaminated with medicine may interfere with the operation of the air pump 45. Air pump 45 could be replaced with an air suction device to reverse the air flow 60 and dispel carbon dioxide by sucking it from the mattress surface 20. For example, in FIG. 1, a reverse flow switch 43 is shown that reverses the direction of the air pump and thus reverses the direction of air flow from pumping to sucking. However, such an arrangement may not be most advantageous if it is desired to either heat or cool the air or add medicine to it.

Figures 2A, 2B:
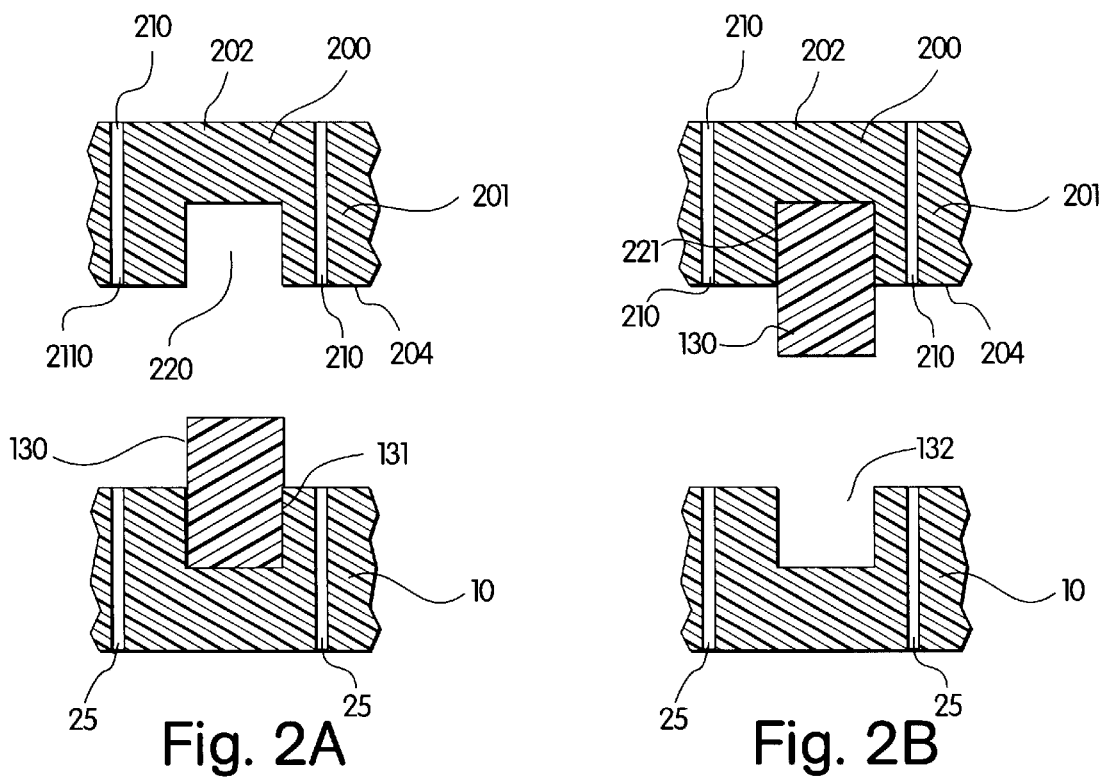
FIG. 2A is a partial cross-sectional side view taken along the line 2—2 of FIG. 1 showing the alignment of the mattress and mattress pad.
FIG. 2B is a partial cross-sectional side view of an alternative embodiment of the alignment feature of the mattress and mattress pad of FIG. 1.

FIG. 1 further shows a plurality of alignment pegs 130 distributed over the mattress surface 20. An enlargement of one such alignment peg 130, situated with respect to a receiving hole in a mattress pad, described below, is shown in FIG. 2A. It is understood that as few as one alignment peg might be used in another embodiment and that the distribution of alignment pegs 130 of this preferred embodiment corresponds to the preferred embodiment of the mattress pad, which, as discussed below, is comprised of separable sections and thus requires alignment pegs to hold each section in place. It is further understood that one or more sections of mattress pad in another embodiment could be held in place without alignment pegs, for example by being fit securely within abutting sections. In the preferred embodiment of FIGS. 1 and 2, alignment pegs 130 are securely inserted into corresponding mattress alignment holes 131 in the mattress surface 20, or they may be molded with the mattress as an extension of mattress surface 20. The alignment pegs 130 extend upwardly away from surface 20 so as to be removably inserted into corresponding mattress pad alignment holes 220 shown in FIGS. 1 and 2.

FIGS. 1 and 2 also illustrate the preferred embodiment of the mattress pad 200 of the invention having a top surface 202 and a bottom surface 204. Pad 200 includes mattress pad air flow holes 210 extending therethrough from surface 202 to surface 204. Pad 200 also includes a plurality of mattress pad alignment holes 220 on the bottom surface 204. Holes 220 extend upwardly into the mattress pad material 201. Holes 220 are adapted to receive alignment pegs 130 shown in FIG. 2A so that the mattress pad air flow holes 210 and passageways 25 are aligned so that the air may flow unimpeded from plenum chamber 22 through passageways 25, through the bottom surface 204 of the mattress pad through mattress pad air flow holes 210, and out top surface 202. It is understood that in another embodiment of the invention, the air flow may be reversed so that a suction device pulls air from the top surface 202 of the mattress pad, through the mattress pad air flow holes 210, through passageways 25, into the plenum 22, and out through the air port 30. In a preferred embodiment, mattress pad 200 may be constructed in a plurality of tiles to facilitate washing, as shown in FIG. 1 as tiles 250, 251, 252, 253, 254, 255, 256, and 257. Each such tile may be separately removed from the mattress and placed in a dishwasher or other washing machine, or washed by hand, and then realigned on the alignment pegs after cleaning.

While in a preferred embodiment, alignment pegs 130 are disposed on upper surface 20 of mattress 10, in an alternative embodiment represented in FIG. 2B, alignment pegs 130 are provided on the lower surface 204 of pad 200. In FIG. 2B, the alignment pegs 130 are securely inserted into corresponding mattress pad alignment holes 221, or they may be molded with the mattress pad as an extension of mattress pad surface 204. In this alternative embodiment, such alignment pegs extend into correspondingly formed alignment holes 132 on the top surface 20 of mattress 10. In either embodiment, the alignment pegs should be formed of a sufficiently flexible material that they will not interfere with movement of the infant on the mattress and will not harm the infant should the infant sit or lie on the pegs. On the other hand, the pegs must be sufficiently rigid so as to provide their alignment function and to prevent movement between pad 200 and mattress surface 20. A preferred material for alignment pegs 130 or the alternative embodiment alignment pegs just noted is an open or closed cell polyester or polyethylene foam, or any other suitable material.

Mattress 10 may be formed of any materials suitable for an infant's mattress. A preferred material is an open or closed cell foam, which can be molded in the desired shape to form upper surface 20 and plenum chamber 22. Suitable materials may include, but are not limited to, styrofoam, epoxy resin foam, foam rubber, polyethylene foam, or polyurethane foam. Typically, such a molded foam mattress will be formed in two parts having a depression in the center. When these two parts are mated around their edges, the mating depressions in each segment of the mattress would form plenum chamber 22. In the preferred embodiment, the molded foam mattress is sufficiently rigid and strong that the weight of the infant on the mattress does not distort the air passageways so as to obstruct the flow of air and does not cause a depression or distortion in the surface of the mattress due to the presence of the plenum chamber. If the mattress is made of a less rigid material in order, for example, to provide a softer surface for the infant, it may be required to insert tubes or other supports in the air passageways, as noted above, or to support the plenum chamber by inserting plastic or other rigid members in or around the chamber.

Figure 4:
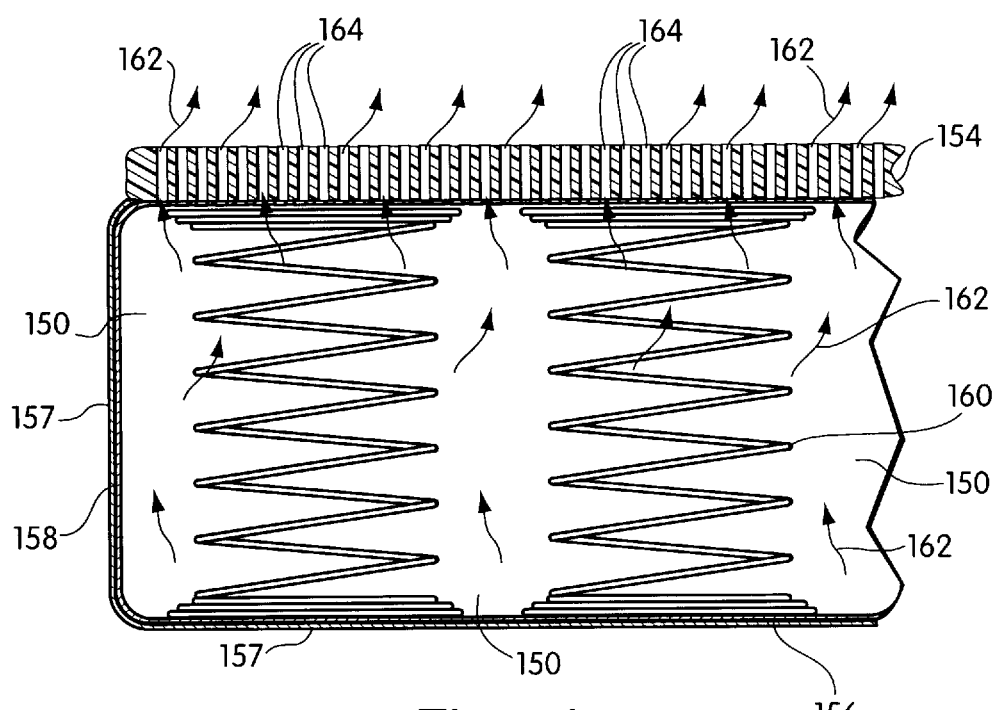
FIG. 4 is a partial cross-sectional side view of another embodiment of the mattress of the present invention.

In an alternative embodiment, mattress 10 may be a conventional spring mattress in which springs are disposed between two covering layers of fabric. In such a spring mattress, a plenum chamber may be a separately formed enclosure (not shown) disposed within the center of the mattress or, with reference to mattress 152 shown in FIG. 4, plenum chamber 150 could even be formed in the unoccupied volume enclosed by top 154, bottom 156, and side panels 158 (only one shown) of mattress 152 between springs 160 and within the volume formed by the spiral configuration of springs 160. Air would enter through an air port (not shown) on any surface of mattress 152 and air flow 162 would proceed through plenum chamber 150, through generally evenly distributed air passageways 164 in top panel 154, and through top panel 154 to the sleeping surface. In such an alternate embodiment, the exterior panels including panels 156 and 158 could form a sealed chamber into which the air is injected and from which air escapes through air passageways 164 in top panel 154 as just described. In another variation, an air impermeable membrane 157, typically made of plastic, could encapsulate all exterior panels except for the top panel to create such sealed chamber. Each of the passageways 164 extends into this sealed chamber 150 and is in gaseous communication therewith. Such a sealed chamber would be most suitable for use with a spring mattress such as mattress 152, as opposed to a molded foam mattress. In yet another embodiment, a sealed container (not shown) may be placed inside the center of the mattress, and each of the holes on the surface of the mattress could be placed in gaseous communication with the container, into which the air is injected.

Figure 3:
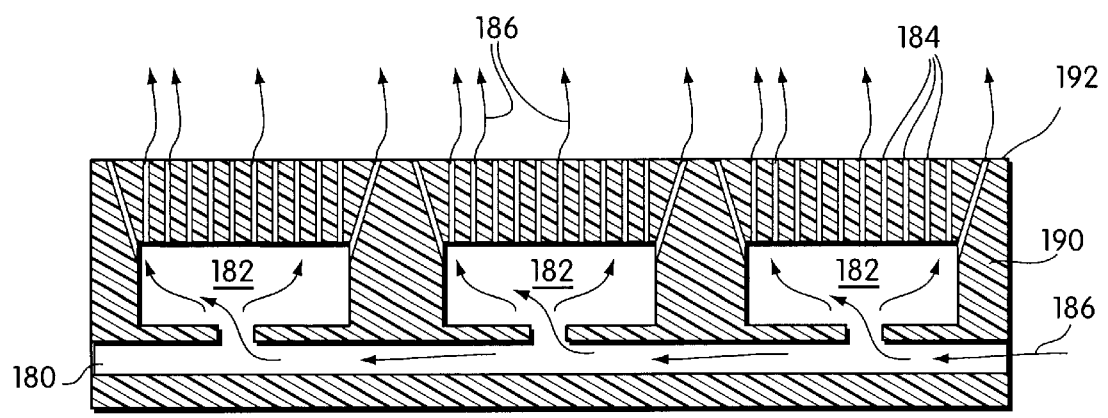
FIG. 3 is a partial cross-sectional side view of another embodiment of the mattress of the present invention.

In other alternative embodiments, a plurality of air ducts (not shown) may be provided coupling each of the passageways 25 to a source of air, or a single tube may be provided that is directly coupled to each of the passageways 25. In yet another embodiment represented in FIG. 3, a manifold 180 connects multiple plenum chambers 182, each of the multiple plenum chambers 182 being gaseously coupled to a predetermined group of passageways 184. Alternatively, multiple plenum chambers 182 may be gaseously connected to a main plenum chamber (not shown). Finally, instead of a plenum chamber, multiple tubes could be attached to a manifold (not shown) which is coupled to a source of air. Each of these tubes would be routed to an air hole and would provide air to that hole. The manifold would provide equal distribution of the air to each of the tubes. Such a manifold could be located either in the center of the mattress or adjacent to hose fitting 32. It is understood that in each of the above-mentioned embodiments, the air could be sucked out of the plenum chamber instead of being inserted therein, thereby withdrawing carbon dioxide from the sleeping surface, and that devices for heating or cooling, or for dispensing medicine, could be provided.

In reference to FIG. 1 or the alternative embodiments just noted, the plenum chamber such as plenum chamber 22 may be produced in various sizes. Typically, the mattress would be molded or formed of a plenum chamber of the desired size to provide a preferred volume and velocity of air through passageways such as passageways 25. For example, the larger is the volume of plenum chamber 22, the greater the volume of air that may be delivered through passageways 25, and vis-a-versa, other factors such as the capacity of the pump and size of air passageways being equal. Typically, the velocity of air would be controlled by a combination of the size of plenum chamber 22 and passageways 25.

In the preferred embodiment of FIGS. 1 and 2, the infant typically may be placed on its stomach on a crib sheet made of a conventional woven fabric (not shown) placed over the mattress pad 200. Alternatively, in an embodiment as noted above in which alignment pegs 130 protrude from the bottom 204 of mattress pad 200 rather than from the mattress surface 20, the mattress pad may be removed and the infant may rest directly on mattress surface 20. As previously noted, alignment of the mattress pad air flow holes 210 and passageways 25 ensure that the air flow, which may be temperature-regulated or medicated in accordance with the operation of the heat canister 50 and medicine canister 55, reach the vicinity of the infant's mouth no matter where the infant is situated in the crib.

Figure 5:
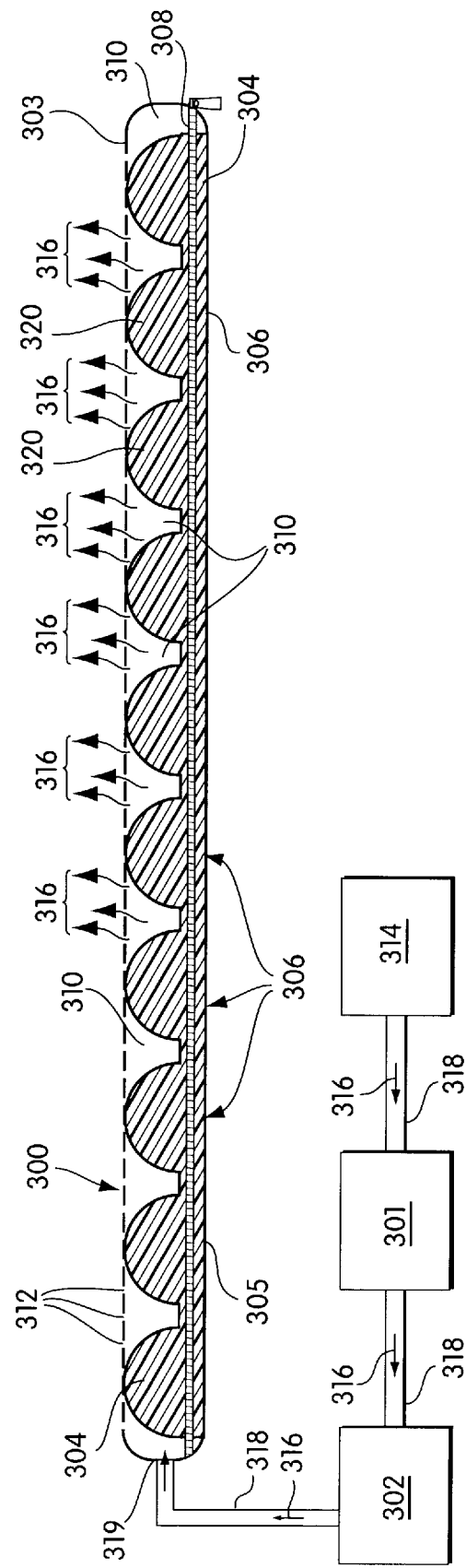
FIG. 5 is a cross-sectional side view of yet another embodiment of a mattress pad of the present invention.
Figure 6:
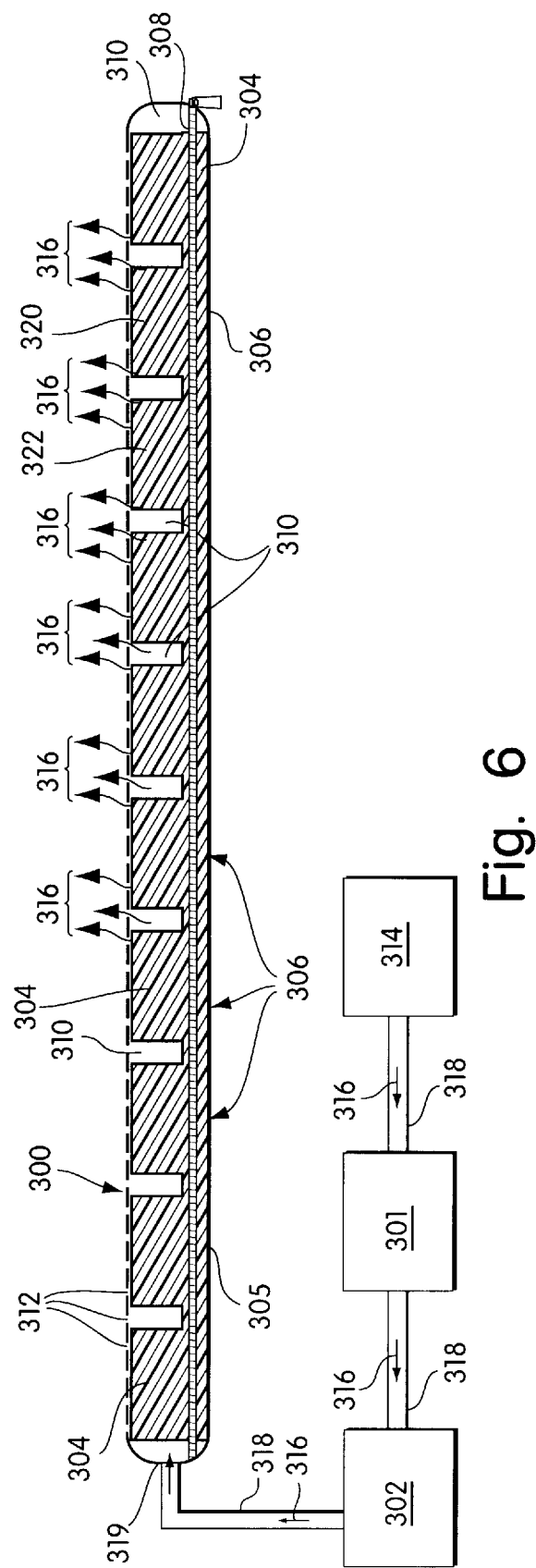
FIG. 6 is cross-sectional side view of an alternative configuration of the mattress pad of FIG. 5.

In yet another preferred embodiment represented in FIGS. 5 to 7, the mattress is itself a mattress pad. A mattress pad cover, or outer membrane of the mattress pad, 300 encloses the top surface and sides of mattress pad 304 and is attached to flaps 305 on the bottom 306 of mattress pad 304 by a zipper 308. It is understood that the outer membrane or cover 300 may alternatively enclose just the top surface of mattress pad 304 and be attached by zipper 308 to flaps 305 on the sides of mattress pad 304, or entirely enclose the mattress pad 304 and be removable by opening zipper 308 on one of its surfaces. A plenum chamber 310 is formed between the upper surface of pad 304 and cover 300. Preferably, pad 304 has raised portions 320 which on its upper surface support cover 300 and the infant. The shape of portions 320 is not critical and may comprise roughly semi-spherical bubbles 320 such as represented in FIGS. 5 and 7, roughly half-cubes such as represented in FIG. 6, or other shapes that allow even distribution of air throughout the plenum chamber 310. The bubbles, cubes, or other shapes may be formed of molded foam or by injecting air or another fluid into the mattress pad 304 having such shapes pre-formed in the material thereof. Thus, for example, the mattress pad 304 may be inflated with air and sealed at the factory so as to create the shape of roughly semi-spherical bubbles 320, or the mattress pad 304 may similarly be inflated and temporarily sealed by the user with a standard sealing apparatus such as an air plug (not shown).

Once removed, the outer membrane 300 may easily be placed in a washing machine or otherwise cleaned, and allows easy access for cleaning of the mattress pad 304. The outer membrane 300 is made of an airtight plastic or other like material that is sufficiently strong to allow air pressure to build up in the plenum chamber 310 and to provide a comfortable and secure sleeping surface, even in the presence of a plurality of generally evenly distributed pinholes 312 that pierce the outer membrane 300 on its top surface 303.

Also with respect to FIGS. 5 to 7, a source of air 314 generates an air flow 316 through a hose 318, through an air port 319 in any surface of the outer membrane 300, into the plenum chamber 310 disposed between the outer membrane 300 and the mattress pad 304, and out the pinholes 312. The source of air 314 maintains a roughly steady pressure in the plenum chamber 310 as the air flow 316 is expelled through the pinholes 312. The preferred embodiment represented by FIGS. 5 through 7 may be placed on a conventional mattress or another flat surface suitable for an infant. Conventional fasteners (not shown), such as straps or adhesive materials, may be used to hold the mattress pad 304 to such conventional mattress or flat surface. As described above with respect to FIG. 1, a heat canister 301 or a medicine canister 302 may be disposed along the air flow 316 between the source of air 314 and mattress pad 304 for heating or cooling air, or for introducing medicinal vapors or medicine, respectively. Also as described above with respect to FIG. 1, it is understood that the arrangement of the source of air 314 and the heat or medicine canister is not crucial.

It is also understood that the invention is suitable for providing air flow, which may be temperature regulated or medicated, to people other than infants. For example, people who are bed ridden due to sickness, surgery, or other reasons may benefit from a sleeping environment that is so regulated or medicated, or that provides an unregulated and unmedicated air flow that is conducive to the healing of skin or prevention of bed sores or the like. Also, the invention is suitable for use by people who prefer the comfort provided by the air flow, temperature regulation, medication, or the soothing noise that may be associated with the air flow.

Having now described the preferred embodiment of the invention, it should be apparent to those skilled in the art that the foregoing is illustrative only and not limiting, having been presented by way of example only. Numerous other embodiments and modifications thereof are contemplated as falling within the scope of the present invention as defined by appended claims and equivalents thereto. By way of illustration rather than limitation, the method and apparatus of the invention may also be readily adapted to providing fresh air, medication, or temperature-controlled air to a resting or sleeping person who is not an infant and thus not in danger of succumbing to SIDS.

What is claimed is:

1. An apparatus for preventing sudden infant death syndrome comprising:

a mattress having a top surface;

a plurality of air passageways generally evenly distributed over substantially all of said top surface of said mattress;

a source of air;

a distribution apparatus disposed between the air passageways and the source of air for generally evenly distributing air from said source of air to each of said air passageways; and a mattress pad disposed on said top surface of said mattress, said mattress pad having a top surface, a bottom surface, and a plurality of holes extending from said top surface to said bottom surface.

2. The apparatus of claim 1 further comprising an alignment element for aligning said holes in said mattress pad with air passageways disposed in said top surface of said mattress.

3. The apparatus of claim 2 wherein said alignment element comprises a hole in said bottom surface of said mattress pad, and a mating peg extending from said top surface of said mattress into said hole in said mattress pad.

4. The apparatus of claim 3 wherein said mattress pad is formed of a plurality of sections which are separable one from the other.

5. An apparatus for preventing sudden infant death syndrome comprising:

a mattress having a top surface, said mattress comprising a lower portion having spaced, raised portions disposed on an upper surface thereof, said top surface of said mattress being formed of a covering material that rests on said raised portions;

a plurality of air passageways generally evenly distributed over substantially all of said top surface of said mattress;

a source of air; and a distribution apparatus disposed between the air passageways and the source of air for generally evenly distributing air from said source of air to each of said air passageways wherein said distribution apparatus comprises a plenum chamber disposed in the interior of the mattress in direct gaseous communication with each of said plurality of air passageways.

6. The apparatus of claim 5 wherein said distribution apparatus comprises said plenum chamber defined by interconnected spaces disposed between said raised portions.

7. The apparatus of claim 5 further comprising an apparatus for connecting and disconnecting said material to and from said mattress pad.

8. The apparatus of claim 5 further comprising a temperature control element disposed in the air flow from said source of air to said plurality of holes in said top surface of said mattress pad cover for selectively heating and cooling air from said source of air.

9. The apparatus of claim 5 further comprising a medicine dispenser disposed in the air flow from said source of air to said plurality of holes in said top surface of said mattress pad cover, said medicine dispenser dispensing medicine into the air flow.

10. A method for preventing sudden infant death syndrome while an infant is disposed on a mattress, said method comprising the steps of:

providing a plurality of air passages over substantially all of an upper surface of the mattress;

directing air from a source of air to each of the air passageways;

regulating the flow of air to said air passageways so that air flows to each of said passageways;

providing a mattress pad covering the top surface of the mattress, the mattress pad having a plurality of holes; and aligning the mattress pad on the top surface of the mattress such that each hold in the mattress pad is aligned substantially with an air passageway in the top surface of the mattress.

11. Apparatus for providing a uniformly distributed flow of air to the top surface of a mattress, said apparatus comprising:

a plurality of air passageways generally evenly distributed over substantially all of the top surface of the mattress;

a source of air;

a distribution apparatus disposed between the air passageways and the source of air for generally evenly distributing the air from the source of air to each of said air passageways;

a mattress pad having a plurality of openings disposed uniformly across the surface of the mattress pad; and an element for aligning each of said holes in said mattress pad with an air passageway in said top surface of said mattress.

12. An apparatus for preventing sudden infant death syndrome comprising:

a mattress formed of a molded unitary construction and having a top surface;

a plurality of air passageways generally evenly distributed over substantially all of said top surface of said mattress;

a source of air;

a distribution apparatus disposed between the air passageways and the source of air for generally evenly distributing air from said source of air to each of said air passageways, wherein said distribution apparatus comprises a chamber molded into an interior of the mattress, the chamber being in direct gaseous communication with each of said plurality of air passageways.

13. The apparatus of claim 12, wherein said molded unitary construction comprises molded foam.

14. The apparatus of claim 12, wherein said molded unitary construction comprises molded plastic.

15. The apparatus of claim 12, wherein said chamber has at least one port in gaseous communication with said source of air, at least one port in direct gaseous communication with each of said plurality of air passageways, and is otherwise sealed.

16. The apparatus of claim 12 further comprising a mattress pad disposed on said top surface of said mattress, said mattress pad having a top surface, a bottom surface, and a plurality of holes extending from said top surface to said bottom surface.

17. The apparatus of claim 16 further comprising an alignment element for aligning said holes in said mattress pad with air passageways disposed in said top surface of said mattress, wherein said alignment element comprises a hole in said bottom surface of said mattress pad, and a mating peg extending from said top surface of said mattress into said hole in said mattress pad.

18. The apparatus of claim 17 wherein said mattress pad is formed of a plurality of sections which are separable one from the other.

19. The apparatus of claim 12 wherein said mattress comprises a lower portion having spaced, raised portions disposed on an upper surface thereof, wherein said top surface of said mattress is formed of a covering material that rests on said raised portions, and wherein said chamber is defined by interconnected spaces disposed between said raised portions.

20. A method for forming a mattress having a top surface and an interior air-distribution chamber, comprising the steps of:

molding an upper portion of the mattress comprising the top surface and having a lower surface opposed to the top surface, the upper portion of the mattress further having an upper chamber extending generally upward from the lower surface, molding a lower portion of the mattress having an upper surface and a lower chamber extending generally downward from the upper surface, mating the lower surface of the upper portion of the mattress to the upper surface of the lower portion of the mattress so that the upper and lower chambers are substantially aligned to form the interior air-distribution chamber, providing air passageways generally evenly distributed over substantially all of the top surface of the mattress, each of the passageways being in direct gaseous communication with the interior air-distribution chamber, and providing a port from the interior air-distribution chamber for gaseous connection external to the mattress.

21. The method of claim 20 further comprising the steps of:

providing a mattress pad covering the top surface of the mattress, the mattress pad having a plurality of holes; and aligning the mattress pad on the top surface of the mattress such that each hole in the mattress pad is aligned substantially with an air passageway in the top surface of the mattress.

* * * * *